United States Patent [19]

Murayama et al.

[11] 3,963,730

[45] June 15, 1976

[54] PROCESS FOR PREPARING TRIACETONAMINE

[75] Inventors: Keisuke Murayama; Syoji Morimura; Takao Yoshioka; Tomoyuki Kurumada, all of Hiromachi, Japan

[73] Assignee: Sankyo Company Limited, Tokyo, Japan

[22] Filed: June 21, 1974

[21] Appl. No.: 481,839

[30] Foreign Application Priority Data

| | | |
|---|---|---|
| June 26, 1973 | Japan | 48-72014 |
| July 16, 1973 | Japan | 48-80200 |
| July 16, 1973 | Japan | 48-80201 |
| July 16, 1973 | Japan | 48-80202 |
| July 16, 1973 | Japan | 48-80203 |
| May 30, 1974 | Japan | 49-61148 |

[52] U.S. Cl. ........................................... 260/293.89
[51] Int. Cl.$^2$ ....................................... C07D 211/74
[58] Field of Search ............................. 260/293.89

[56] References Cited
UNITED STATES PATENTS

3,513,170　5/1970　Murayama et al............. 260/294.7

*Primary Examiner*—G. Thomas Todd
*Attorney, Agent, or Firm*—Toren, McGeady and Stanger

[57] ABSTRACT

A process for preparing triacetonamine, characterized in that acetonine is reacted with acetone in the presence of at least 12.5 mol % based on acetonine of an acid catalyst under anhydrous conditions. Triacetonamine is used as an intermediate for light stabilizer for synthetic polymers.

44 Claims, No Drawings

PROCESS FOR PREPARING TRIACETONAMINE

This invention relates to a novel process for preparing triacetonamine having the structure expressed by the following formula:

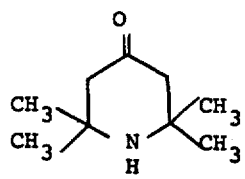

(I)

More particularly, the invention relates to an improved process for preparing triacetonamine from acetonine having the structure expressed by the following formula:

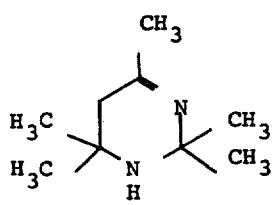

(II)

It is known that a process comprising contacting acetonine with water in the presence of a Lewis acid (Japanese Patent Publication No. 12141/1969) is most excellent among conventional processes for the preparation of triacetonamine. Even this process, however, is still insufficient in that the yield of the intended product is about 60 % at the highest and resinous substances containing Lewis acids used for the reaction, such as calcium chloride and zinc chloride, are formed as by-products in large quantities, for disposal of which complicated means inclusive of pollution-preventive treatments have to be adopted. Thus, this process still includes problems to be solved.

As a result of research works with a view to overcoming the above defects included in such conventional process, the inventors have found that the foregoing problems can be solved by adopting a technique quite different from the conventional ones. Based on this finding, we have now completed this invention.

The process of the present invention comprises reacting acetonine with acetone and/or diacetone alcohol in the presence of at least 12.5 mol % based on acetonine of an acid catalyst under anhydrous conditions. Preferably in the process according to the invention acetonine is reacted with acetone in the presence of the acid catalyst.

The acid catalyst which may be used in the process according to the invention, there can be mentioned a salt of a proton acid with ammonia or a nitrogen-containing organic base.

As the proton acid which may be used for the formation of such salts, mineral acids or organic acids such as e.g., organic phosphorus-oxygen acids, organic sulfur-oxygen acids, especially sulfonic acids, or carboxylic acids may be mentioned.

As the mineral acid, there can be mentioned hydrohalogen acids, e.g., hydrochloric, hydrobromic or hydroiodic acid, nitric acid and phosphoric acid.

As the carboxylic acid, there can be mentioned monobasic, dibasic and tribasic aliphatic and aromatic carboxylic acids. For instance, there can be employed saturated and unsaturated monobasic aliphatic acids having preferably from 1 to 18 carbon atoms, such as formic acid, acetic acid, propionic acid, butyric acid, lauric acid, palmitic acid, stearic acid, acrylic acid, methacrylic acid, halogen-containing carboxylic acids such as chloroacetic, dichloroacetic or trichloroacetic acid and trifluoroacetic acid, saturated and unsaturated dibasic aliphatic carboxylic acids having preferably from 2 to 12 carbon atoms such as malonic acid, succinic acid, adipic acid, sebacic acid, tartaric acid, malic acid, fumaric acid, and maleic acid, tribasic aliphatic carboxylic acids such as citric acid, monobasic optionally substituted aromatic carboxylic acids such as, benzoic acid, toluic acid, cinnamic acid and naphthoic acid, dibasic aromatic carboxylic acids such as phthalic acid and terephthalic acid, and tribasic aromatic carboxylic acids such as trimellitic acid.

As organic sulfur-oxygen acids, there may be mentioned alkylsulfuric acids, such as methylsulfuric acid, sulfinic acids, such as benzenesulfinic acids, but especially sulfonic acids.

As the sulfonic acid, there can be mentioned aliphatic and optionally substituted aromatic sulfonic acids such as methanesulfonic acid, benzenesulfonic acid, p-toluenesulfonic acid, naphthalenesulfonic acid and naphthalene-1,5-disulfonic acid.

As organic phosphorus-oxygen acids, there may be mentioned aliphatic or aromatic phosphonic or phosphinic acids, such as methyl-, benzyl- or phenylphosphonic acid or dimethyl- or diethylphosphonic acid or diethyl- or benzenephosphinic acid.

As the nitrogen-containing organic base, there can be mentioned, aliphatic, alicyclic and aromatic primary, secondary and tertiary amines, saturated and unsaturated nitrogen-containing heterocyclic bases, urea, thiourea and basic ion-exchange resins.

For instance, there can be employed aliphatic primary amines having preferably from 1 to 18 carbon atoms, such as methylamine, ethylamine, n-butylamine, octylamine, dodecylamine and hexamethylenediamine, aliphatic secondary amines having preferably from 2 to 16 carbon atoms, such as dimethylamine, diethylamine, di-n-propylamine and di-isobutylamine, aliphatic tertiary amines such as triethylamine, alicyclic primary amines such as cyclohexylamine, alicyclic secondary amines such as dicyclohexylamine, optionally substituted aromatic primary amines such as aniline, toluidine, naphthylamine and benzidine, aromatic secondary amines such as N-methylaniline and diphenylamine, aromatic tertiary amines such as N,N-diethylaniline, saturated and unsaturated, nitrogen-containing heterocyclic bases such as pyrrolidine, piperidine, N-methyl-2-pyrrolidone, pyrazolidine, piperazine, pyridine, picoline, indoline, quinuclidine, morpholine, N-methylmorpholine, 1,4-diazabicyclo[2,2,-2]octane, acetonine, and triacetonamine, urea, thiourea, and highly basic and weakly basic ion-exchange resins, such as Amberlites IR-45 and IRP-58 (Products of Rhom and Haas Co.).

As the preferred ammonium salts of mineral acids, there are mentioned ammonium halides, e.g. ammonium chloride, ammonium bromide or ammonium iodide, ammonium nitrate and ammonium borate.

As the preferred ammonium salts of organic acids, there are mentioned ammonium salts of monobasic and dibasic lower aliphatic carboxylic acids or monobasic aromatic sulfonic acids such as ammonium formate, ammonium acetate, ammonium di- and trichloroacetate, ammonium trifluoroacetate, ammonium malonate, ammonium benzoate and ammonium p-toluenesulfonate.

As the preferred salts of nitrogen-containing organic bases with mineral acids, there are mentioned methylamine hydrochloride, cyclohexylamine hydrochloride, hexamethylenediamine dihydrochloride, aniline hydrochloride, p-nitroaniline hydrochloride, dimethylamine hydrochloride, diphenylamine hydrochloride, diisobutylamine hydrochloride, triethylamine hydrochloride, triethylamine hydrobromide, 1,4-diazabicyclo[2,2,2]octane monohydrochloride, triacetonamine hydrochloride, triacetonamine sulfate, urea nitrate, thiourea hydrochloride and hydrochloric acid-treated basic ion-exchange resins.

As the preferred salts of nitrogen-containing organic bases with organic acids, there are mentioned cyclohexylamine formate, pyridine formate, pyridine p-toluenesulfonate, di-n-butylamine acetate, di-n-butylamine benzoate, morpholine succinate, morpholine maleate, triethylamine acetate, triethylamine succinate, triethylamine maleate, aniline acetate and triacetonamine p-toluenesulfonate.

Especially preferred nitrogen-containing organic bases forming such salts are triacetonamine, triethylamine, hexamethylenediamine, 1,4-diazabicyclo[2,2,-2]octane, urea or thiourea.

Especially advantageous proton acids for forming such salts are hydrochloric, hydrobromic, hydroiodic, nitric, halogenoacetic or organic sulfonic acid.

Especially good results are obtained by using ammonium salts or salts of the above especially preferred nitrogen-containing organic bases with hydrochloric acid, hydrobromic acid, hydroiodic acid, nitric acid, benzenesulfonic acid, p-toluenesulfonic acid, methanesulfonic acid, dichloroacetic acid or trichloroacetic acid.

Most preferred is the use as catalyst of ammonium chloride, ammonium bromide, ammonium iodide, ammonium formate, ammonium tosylate, triacetoneamine hydrochloride, urea nitrate, urea tosylate, thiourea hydrochloride and hexamethylenediamine dihydrochloride, particularly the use of hexamethylenediamine dihydrochloride.

Further, acid catalysts which may be used in the process according to the present invention may be an acid.

As the acid, there may be mentioned Lewis acid such as aluminum chloride, tin chloride, zinc chloride and calcium chloride, iodine, bromine, preferably boron trifluoride.

As the acid, there may be mentioned a proton acid.

As proton acid, there can be used above mentioned mineral acids or organic acids such as e.g. organic phosphorus-oxygen acids, oganic sulfur-oxygen acids, especially sulfonic or carboxylic acids.

Preferred examples of the organic acid are monobasic and dibasic aliphatic and aromatic carboxylic acid and monobasic aromatic sulfonic acid.

Most preferred examples of the proton acid are hydrochloric acid, formic, acetic, malonic, succinic, maleic, benzoic or cinnamic acid and benzenesulfonic or p-toluenesulfonic acid.

A preferred embodiment of the invention is to use the acid in a stoichiometric ratio to the acetonine.

Therefore, the invention comprises reacting an acid adduct salt of acetonine with diacetone alcohol and/or preferably acetone under anhydrous conditions.

As the acid adduct salt of acetonine, there can be mentioned adducts with proton acids, preferably such as mineral acid salts and salts with organic acids, e.g., carboxylic acid salts and sulfonic acid salts of acetonine are used.

As the mineral acids, carboxylic acids and sulfonic acids, there can be employed such acids as mentioned above.

Preferred examples of the acid adduct salts of acetonine are monobasic and dibasic aliphatic acid salts of acetonine and monobasic aromatic sulfonic acid salts of acetonine.

Most preferred examples of the acid adduct salts of acetonine include acetonine hydrochloride, acetonine formate, acetonine acetate, acetonine malonate, acetonine succinate, acetonine maleate, acetonine benzoate, acetonine cinnamate, acetonine benzenesulfonate and acetonine p-toluenesulfonate.

The inventors have found that an acid adduct salts of acetonine can be formed sustantially quantitatively by reacting acetonine (II) with a stoichiometric amount of an acid in the presence of an organic solvent at a low temperature and that the acid adduct salt per se is relatively stable.

The inventors have further found that triacetonamine can be obtained unexpectedly in a high yield by reacting the acid adduct salt of acetonine taken out from the reaction liquor or kept in the reaction liquor with acetone and/or diacetone alcohol, optionally in the presence of an organic solvent, i.e. in the form of a solution or suspension in the organic solvent. Most preferred as coreactant is acetone.

A particularly important feature of the present invention resides, therefore, in the use of an acid adduct salt of acetonine as a starting material. Organic solvents used in the preparation of an acid adduct salt of acetonine are those inert to the reaction and containing no water such as aromatic hydrocarbons, for example, benzene, toluene and xylene; and ketones, for example, acetone; and alcohols, for example, methanol and ethanol. Reaction is carried out at a temperature kept in the range of 0° – 10°C., preferably 0° – 5°C. The acids are used in a stoichiometric amount based on acetonine. Acids used therefore may be proton acids.

Preferred proton acids are mineral acids, or organic acids such as carboxylic acids and sulfonic acids, particularly hydrohalogenic acid, sulfuric acid, nitric acid, phosphoric acid, formic acid, acetic acid, chloroacetic acid, dichloroacetic acid, trichloroacetic acid, trifluoroacetic acid, maleic acid, succinic acid, malonic acid, benzoic acid, cinnamic acid, and aromatic and aliphatic sulfonic acids. Most preferably, hydrochloric acid, formic acid, acetic acid, maleic acid, succinic acid, malonic acid, benzoic acid, cinnamic acid, p-toluenesulfonic acid and benzenesulfonic acid are used. The acid adduct salt of acetonine is generally obtained in the form of crystal precipitated in the solvent used or in the form of solution in the solvent.

The process according to the invention may be preformed at variable temperatures, e.g., from 0°– 150°C., 30° – 150°C., 50° – 100°C. and preferably at 10° – 110°C., especially 20° – 65°C.

Optionally, the reaction is performed by applying pressure either by performing the reaction in a closed system per se or by applying external pressure. The pressure range may extend from 1 to 30 atmospheres, especially from 1 to 10 atmospheres, most preferably from 1 to 3 atmospheres.

Although the use of a solvent is not particularly indispensable in practicing the process of this invention, it is advantageous to perform the reaction in the presence of an organic solvent.

As organic solvents, there may be used, for instance, aliphatic or aromatic, optionally halogenated hydrocarbons, e.g., hexane, heptane, cyclohexane, benzene, toluene, xylene, methylene chloride, chloroform, carbon tetrachloride, trichloroethylene or chlorobenzene; substituted or unsubstituted aliphatic mono- or polyfunctional alcohols, e.g., methanol, ethanol, propanol, isopropanol, butanol, octanol, cyclohexanol, benzyl alcohol, ethylene glycol monomethyl ether or glycol; ethers, e.g., dioxane, tetrahydrofuran or diethyl ether; esters, e.g., ethyl acetate; aprotic polar solvents, e.g., dimethylformamide, dimethylacetamide, dimethylsulfoxide, tetramethylurea, hexamethylphosphoric acid amide, sulfolane, acetonitrile or nitromethane.

Preferred is the use of lower alcohols having from 1 to 4 carbon atoms or ethylene glycol monomethylether. Most advantageously methanol or ethanol or a mixture thereof is used as a solvent.

The reaction should be carried out under anhydrous conditions, However, since the presence of such water as contained in ordinarily called "anhydrous" solvent, starting compound and reagent and contained in air has no significant influence, commercially available anhydrous solvents and reagents may be used as such without conducting a particular dehydrating treatment.

Triacetonamine is usually obtained in yields of more than 85%. Especially high yields are obtained by employing an ammonium salt as catalyst in a molar excess amount based on acetonine in the presence of acetone.

The yields of the process according to the invention may also be improved and the reaction time shortened by adding, in addition to the acid catalyst, 0.01 to 0.5 mol % based on acetonine of another catalyst selected from the group consisting of bromine, iodine, sodium iodide, potassium iodide, lithium iodide, lithium bromide, lithium thiocyanate, ammonium thiocyanate, lithium cyanide, lithium nitrate or ammonium sulfide or the bromide, iodide, nitrate, methanesulfonate, benzenesulfonate or tosylate of ammonia, triethylamine, urea or thiourea.

The reaction time varies deponding on the reaction conditions and the kind of the catalyst used. In general, the reaction is completed within several hours to ten and several hours. After termination of the reaction, the intended product, triacetonamine, is collected from the reaction mixture according to customary procedures. For instance, after termination of the reaction, excess amount of acetone and/or diacetone alcohol and the solvent is distilled off under reduced pressure, water is added to the residue, the mixture is made alkaline, extraction is effected with a suitable solvent, the solvent is distilled off from the extract, and the residue is subjected to vaccum distillation, whereby the intended product can be recovered in a pure form. By-products of the reaction are present in only small amounts and, therefore, the purification of the final product and removal of the by-products are easy.

Thus, as compared with the conventional processes, the process of the present invention is a quite excellent process for preparing triacetonamine on a commercial scale.

The industrial value of the process is quite high, since triacetonamine and especially its derivatives are used in a large amount as photostabilizers for polymeric materials and as starting materials for the synthesis of pharmaceuticals.

The process of the present invention is illustrated by the following examples.

EXAMPLE 1.

2.4 g. of Ammonium chloride was added to a solution of 6.7 g. of acetonine in 20 ml. of acetone and the mixture was heated to 60°C. under reflux for 10 hours. Then, acetone was distilled out. The resulting reaction mixture was added with saturated aqueous potassium carbonate solution and subjected to extraction with benzene. The extract was dried over anhydrous potassium carbonate. Benzene was distilled off and the residue was purified by distillation under reduced pressure to obtain 6.1 g. of triacetonamine in the form of pale yellow liquid boiling at 75°–76°C./4 mmHg. Upon cooling, the liquid grew into crystals melting at 35°–36°C. Yield, 91.1%.

EXAMPLE 2.

26 ml. of Benzene and 1.0 g. of ammonium chloride were added to a solution of 10.0 g. of acetonine in 10.3 g. of acetone and the mixture was heated to 63°C. under reflux for 21 hours. Then, benzene as solvent and excessive acetone were distilled out. The resulting reaction mixture was added with saturated aqueous potassium carbonate solution and subjected to extraction with benzene. The extract was dried over anhydrous potassium carbonate. Benzene was distilled off and the residue was purified by distillation under reduced pressure to obtain 8.5 g. of triacetonamine in the form of pale yellow liquid boiling at 75°–76°C./4 mmHg. Upon cooling, the liquid grew into crystals melting at 35°–36°C. Yield, 85%.

EXAMPLE 3.

6.4 g. of Ammonium bromide was added to a solution of 10 g. of acetonine in 30 ml. of acetone and the mixture was heated to 60°C. under reflux for 12 hours. Then acetone was distilled out. The resulting reaction mixture was added with saturated potassium carbonate solution and subjected to extraction with benzene. The extract was dried over anhydrous potassium carbonate. Benzene was distilled off and the residue was purified by distillation under reduced pressure to obtain 9.0 g. of triacetonamine in the form of pale yellow liquid boiling at 75°–76°C./4 mmHg. Upon cooling, the liquid grew into crystals melting at 35°–36°C. Yield, 90%.

EXAMPLE 4.

9.5 g. of Ammonium iodide was added to a solution of 10 g. of acetonine in 30 ml. of acetone and the mixture was heated to 60°C. under reflux for 12 hours. Then, acetone was distilled out. The resulting reaction mixture was added with saturated aqueous potassium carbonate solution and subjected to extraction with benzene. The extract was dried over anhydrous potassium carbonate. Benzene was distilled off and the residue was purified by distillation under reduced pressure to obtain 8.9 g. of triacetonamine in the form of pale yellow liquid boiling at 75°–76°C./4 mmHg. Upon cooling, the liquid grew into crystals melting at 35°–36°C. Yield, 89%.

EXAMPLE 5.

6.0 g. of Ammonium nitrate was added to a solution of 10 g. of acetonine in 30 ml. of acetone and the mixture was heated to 60°C. under reflux for 12 hours. Then, acetone was distilled out. The resulting reaction mixture was added with saturated aqueous potassium carbonate solution and subjected to extraction with benzene. The extract was dried over anhydrous potassium carbonate. Benzene was distilled off and the residue was purified by distillation under reduced pressure to obtain 8.6 g. of triacetonamine in the form of pale yellow liquid boiling at 75°–76°C./4 mmHg. Upon cooling, the liquid grew into crystals melting at 35°–36°C. Yield, 86%.

EXAMPLE 6.

6.2 g. of Ammonium borate was added to a solution of 10 g. of acetonine in 30 ml. of acetone and the mixture was heated to 60°C. under reflux for 12 hours. Then, acetone was distilled out. The resulting reaction mixture was added with saturated aqueous potassium carbonate solution and subjected to extraction with benzene. The extract was dried over anhydrous potassium carbonate. Benzene was distilled off and the residue was purified by distillation under reduced pressure to obtain 8.5 g. of triacetonamine in the form of pale yellow liquid boiling at 75°–76°C./4 mmHg. Upon cooling, the liquid grew into crystals melting at 35°–36°C. Yield, 85%.

EXAMPLE 7.

40 ml. of Acetone was added to 15.4 g. of acetonine and 7.0 g. of ammonium formate, and the mixture was heated under reflux at 60°C. for 13 hours. Then, the acetone was distilled off. A saturated aqueous solution of potassium carbonate was added to the reaction mixture, and the resulting mixture was extracted with benzene. The extract was dried over anhydrous potassium carbonate and benzene was distilled off. The residue was purified by distillation under reduced pressure to obtain 14.9 g. of triacetonamine in the form of pale yellow liquid boiling at 75°–76°C./4 mmHg. Upon cooling the liquid grew into crystals melting at 35°–36°C. Yield, 96%.

EXAMPLE 8.

40 ml. of Acetone was added to 15.4 g. of acetonine and 8.0 g. of ammonium acetate, and the mixture was heated under reflux at 60°C. for 13 hours. Then, the acetone was distilled off. The resulting reaction mixture was purified in the same manner as in Example 1 to obtain 13.2 g. of triacetonamine. Yield, 85%.

EXAMPLE 9.

40 ml. of Acetone was added to 15.4 g. of acetonine and 7.1 g. of diammonium malonate, and the mixture was heated under reflux at 60°C. for 13 hours. The acetone was distilled off. The resulting reaction mixture was purified in the same manner as in Example 1 to obtain 13. 7 g. of triacetonamine. Yield, 90%.

EXAMPLE 10.

45 ml. of Acetone was added to 15.4 g. of acetonine and 13.8 g. of diammonium malonate, and the mixture was heated under reflux at 60°C. for 13 hours. The acetone was distilled off. The resulting reaction mixture was purified in the same manner as in Example 1 to obtain 13.5 g. of triacetonamine. Yield, 87%.

EXAMPLE 11.

40 ml. of Acetone was added to 15.4 g. of acetonine and 7.8 g. of diammonium succinate, and the mixture was heated under reflux at 60°C. for 13 hours. The acetone was distilled off. The resulting reaction mixture was purified in the same manner as in Example 1 to obtain 13.2 g. of triacetonamine. Yield, 85%.

EXAMPLE 12.

40 ml. of Acetone was added to 15.4 g. of acetonine and 14.3 g. of ammonium benzoate, and the mixture was heated under reflux at 60°C. for 13 hours. The acetone was distilled off. The resulting reaction mixture was treated in the same manner as in Example 1 to obtain 13.8 g. of triacetonamine. Yield, 89%.

EXAMPLE 13.

60 ml. of Acetone was added to 15.4 g. of acetonine and 19.2 g. of ammonium p-toluenesulfonate, and the mixture was heated under reflux at 60°C. for 13 hours. The acetone was distilled off. The resulting reaction mixture was purified in the same manner as in Example 1 to obtain 14.6 g. of triacetonamine. Yield, 94%.

EXAMPLE 14.

40 ml. of Acetone was added to 10.0 g. of acetonine and 11.0 g. of cyclohexylamine formate, and the mixture was heated under reflux at 70°C. for 13 hours. Then, the acetone was distilled off, and a saturated aqueous solution of potassium carbonate was added to the resulting reaction mixture. Then, the mixture was extracted with benzene, and the extract was dried over anhydrous potassium carbonate. Benzene was distilled off, and the residue was purified by distillation under reduced pressure to obtain 8.5 g. of triacetonamine in the form of pale yellow liquid boiling at 75°–76°C./4 mmHg. Upon cooling, the liquid grew into crystals melting at 35°–36°C. Yield, 85%.

EXAMPLE 15.

40 ml. of Acetone was added to 10.0 g. of acetonine and 10.2 g. of pyridine formate, and the mixture was heated under reflux at 60°C. for 13 hours. Then, the acetone was distilled off, and the resulting reaction mixture was purified in the same manner as in Example 1 to obtain 8.9 g. of triacetonamine in the form of pale yellow liquid boiling at 75°–76°C./4 mmHg. Upon cooling, the liquid grew into crystals melting at 35°–36°C. Yield, 89%.

EXAMPLE 16.

40 ml. of Acetone was added to 10.0 g. of acetonine and 14.5 g. of di-n-butylamine acetate, and the mixture was heated under reflux at 70°C. for 13 hours. Then, the acetone was distilled off, and the resulting reaction mixture was purified in the same manner as in Example 1 to obtain 8.6 g. of triacetonamine. Yield, 86%.

EXAMPLE 17.

40 ml. of Acetone was added to 10.0 g. of acetonine and 18.1 g. of aniline acetate, and the mixture was heated under reflux at 60°C. for 13 hours. Then, the acetone was distilled off, and the resulting reaction mixture was purified in the same manner as in Example 1 to obtain 8.6 g. of triacetonamine. Yield, 86%.

EXAMPLE 18.

40 ml. of Acetone was added to 10.0 g. of acetonine and 15.7 g. of morpholine succinate, and the mixture was heated under reflux at 60°C. for 13 hours. The acetone was distilled off, and the resulting reaction mixture was purified in the same manner as in Example 1 to obtain 8.5 g. of triacetonamine. Yield, 85%.

EXAMPLE 19.

45 ml. of Acetone was added to 10.0 g. of acetonine and 10.8 g. of triethylamine succinate, and the mixture was heated under reflux at 60°C. for 13 hours. Then, the acetone was distilled off, and the resulting reaction mixture was purified in the same manner as in Example 1 to obtain 8.6 g. of triacetonamine. Yield, 86%.

EXAMPLE 20.

45 ml. of Acetone was added to 10.0 g. of acetonine and 15.7 g. of morpholine maleate, and the mixture was heated under reflux at 60°C. for 13 hours. Then, the acetone was distilled off, and the resulting reaction mixture was purified in the same manner as in Example 1 to obtain 8.5 g. of triacetonamine. Yield, 85%.

EXAMPLE 21.

45 ml. of Acetone was added to 10.0 g. of acetonine and 16.7 g. of triethylamine maleate, and the mixture was heated under reflux at 60°C. for 13 hours. Then, the acetone was distilled off, and the resulting reaction mixture was purified in the same manner as in Example 1 to obtain 9.3 g. of triacetonamine. Yield, 93%.

EXAMPLE 22.

60 ml. of Acetone was added to 10.0 g. of acetonine and 19.2 g. of di-n-butylamine benzoate, and the mixture was heated under reflux at 60°C. for 13 hours. Then, the acetone was distilled off, and the resulting reaction mixture was purified in the same manner as in Example 1 to obtain 8.5 g. of triacetonamine. Yield, 85%.

EXAMPLE 23.

60 ml. of Acetone was added to 10.0 g. of acetonine and 20.6 g. of pyridine p-toluenesulfonate, and the mixture was heated under reflux at 60°C. for 13 hours. Then, the acetone was distilled off, and the resulting reaction mixture was purified in the same manner as in Example 1 to obtain 8.8 g. of triacetonamine. Yield, 88%.

EXAMPLE 24.

11.3 g. of Acetone and 50 ml. of benzene were added to 10.0 g. of acetonine and 20.6 g. of pyridine p-toluenesulfonate, and the mixture was heated under reflux at 60°C. for 13 hours. Benzene was distilled off, and the resulting reaction mixture was purified in the same manner as in Example 1 to obtain 8.5 g. of triacetonamine. Yield, 85%.

EXAMPLE 25.

11.3 g. of Acetone and 50 ml. of benzene were added to 10.0 g. of acetonine and 3.0 g. of triethylamine acetate, and the mixture was heated under reflux at 60°C. for 13 hours. Benzene was distilled off, and the resulting reaction mixture was purified in the same manner as in Example 1 to obtain 8.5 g. of triacetonamine. Yield, 85%.

EXAMPLE 26.

90 ml. of Acetone was added to 15.4 g. of acetonine, and 32.7 g. of triacetonamine p-toluenesulfonate, and the mixture was heated under reflux at 60°C. for 13 hours. Then, the acetone was distilled off, and the resulting reaction mixture was purified in the same manner as in Example 1 to obtain 29.0 g. of triacetonamine. Yield, 87%.

EXAMPLE 27.

40 ml. of Acetone was added to 15.4 g. of acetonine and 6.8 g. of methylamine hydrochloride and the mixture was heated under reflux at 60°C. for 13 hours. Then, the acetone was distilled off. A saturated aqueous solution of potassium carbonate was added to the reaction mixture, and the resulting mixture was extracted with benzene. The extract was dried over anhydrous potassium carbonate and benzene was distilled off. The residue was purified by distillation under reduced pressure to obtain 13.4 g. of triacetonamine in the form of pale yellow liquid boiling at 75°–76°C./4 mmHg. Upon cooling, the liquid grew into crystals melting at 35°–36°C. Yield, 86%.

EXAMPLE 28.

40 ml. of Acetone was added to 15.4 g. of acetonine and 13.8 g. of cyclohexylamine hydrochloride, and the mixture was heated under reflux at 60°C. for 13 hours. Then, the acetone was distilled off. The resulting reaction mixture was purified in the same manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 85%.

EXAMPLE 29.

40 ml. of Acetone was added to 15.4 g. of acetonine and 13.8 g. of hexamethylenediamine dihydrochloride, and the mixture was heated under reflux at 60°C. for 13 hours. Then, the acetone was distilled off. The resulting reaction mixture was purified in the same manner as in Example 1 to obtain 15.0 g. of triacetonamine in the form of pale yellow liquid boiling at 75°–76°C./4 mmHg. Upon cooling, the liquid grew into crystals melting at 35°–36°C. Yield, 97%.

EXAMPLE 30.

40 ml. of Acetone was added to 15.4 g. of acetonine and 13.2 g. of aniline hydrochloride, and the mixture was heated under reflux at 60°C. for 13 hours. Then, the acetone was distilled off, and the resulting reaction mixture was purified in the same manner as in Example 1 to obtain 13.2 g. of the intended product in the form of pale yellow liquid boiling at 75°–76°C./ 4 mmHg. Upon cooling, the liquid grew into crystals melting at 35°–36°C. Yield, 85%.

EXAMPLE 31.

40 ml. of Acetone was added to 15.4 g. of acetonine and 18.1 g. of p-nitroaniline hydrochloride, and the mixture was heated under reflux at 60°C. for 13 hours. Then, the acetone was distilled off, and the resulting reaction mixture was purified in the same manner as in Example 1 to obtain 13.5 g. of the intended product in the form of pale yellow liquid boiling at 75°–76°C./4 mmHg. Upon cooling, the liquid grew into crystals melting at 35°–36°C. Yield, 87%.

EXAMPLE 32.

40 ml. of Acetone was added to 15.4 g. of acetonine and 8.6 g. of dimethylamine hydrochloride, and the mixture was heated under reflux at 60°C. for 13 hours. Then, the acetone was distilled off, and the resulting reaction mixture was purified in the same manner as in Example 1 to obtain 13.9 g. of the intended product in the form of pale yellow liquid boiling at 75°–76°C./4 mmHg. Yield, 90%.

EXAMPLE 33.

50 ml. of Acetone was added to 15.4 g. of acetonine and 16.3 g. of dimethylamine hydrochloride, and the mixture was heated under reflux at 60°C. for 13 hours. Then, the acetone was distilled off, and the resulting reaction mixture was purified in the same manner as in Example 1 to obtain 13.7 g. of the intended product in the form of pale yellow liquid boiling at 75°–76°C./4 mmHg. Upon cooling, the liquid grew into crystals melting at 35°–36°C. Yield, 88%.

EXAMPLE 34.

60 ml. of Acetone was added to 15.4 g. of acetonine and 20.7 g. of diphenylamine hydrochloride, and the mixture was heated under reflux at 60°C. for 13 hours. Then, the acetone was distilled off, and the resulting reaction mixture was purified in the same manner as in Example 1 to obtain 13.7 g. of the intended product in the form of pale yellow liquid boiling at 75°–76°C./4 mmHg. Upon cooling, the liquid grew into crystals melting at 35°–36°C. Yield, 88%.

EXAMPLE 35.

40 ml. of Acetone was added to 15.4 g. of acetonine and 17.0 g. of di-isobutylamine hydrochloride, and the mixture was heated under reflux at 60°C. for 13 hours. Then, the acetone was distilled off, and the resulting reaction mixture was purified in the same manner as in Example 1 to obtain 15.2 g. of the intended product in the form of pale yellow liquid boiling at 75°–76°C./4 mmHg. Upon cooling, the liquid grew into crystals melting at 35°–36°C. Yield, 98%.

EXAMPLE 36.

40 ml. of Acetone was added to 15.4 g. of acetonine and 14.2 g. of triethylamine hydrochloride, and the mixture was heated under reflux at 60°C. for 13 hours. Then, the acetone was distilled off, the resulting reaction mixture was purified in the same manner as in Example 1 to obtain 15.0 g. of the intended product in the form of pale yellow liquid boiling at 75°–76°C./4 mmHg. Upon cooling, the liquid grew into crystals melting at 35°–36°C. Yield, 97%.

EXAMPLE 37.

50 ml. of Acetone was added to 15.4 g. of acetonine and 18.2 g. of triethylamine hydrobromide, and the mixture was heated under reflux at 60°C. for 13 hours. Then, the acetone was distilled off, and the resulting reaction mixture was purified in the same manner as in Example 1 to obtain 15.0 g. of the intended product in the form of pale yellow liquid boiling at 75°–76°C./4 mmHg. Upon cooling, the liquid grew into crystals melting at 35°–36°C. Yield, 97%.

EXAMPLE 38.

40 ml. of Acetone was added to 15.4 g. of acetonine and 15.2 g. of 1,4-diazabicyclo[2,2,2]octane monohydrochloride, and the mixture was heated under reflux at 60°C. for 13 hours. Then, the acetone was distilled off, and the resulting reaction mixture was purified in the same manner as in Example 1 to obtain 13.6 g. of the intended product in the form of pale yellow liquid boiling at 75°–76°C./4 mmHg. Upon cooling, the liquid grew into crystals melting at 35°–36°C. Yield, 88%.

EXAMPLE 39.

60 ml. of Acetone was added to 15.4 g. of acetonine and 21.0 g. of 1,4-diazabicyclo[2,2,2]octane sulfate, and the mixture was heated under reflux at 60°C. for 13 hours. Then, the acetone was distilled off, and the resulting reaction mixture was purified in the same manner as in Example 1 to obtain 13.3 g. of the intended product in the form of pale yellow liquid boiling at 75°–76°C./4 mmHg. Upon cooling, the liquid grew into crystals melting at 35°–36°C. Yield, 86%.

EXAMPLE 40.

40 ml. of Acetone was added to 15.4 g. of acetonine and 12.3 g. of pyridine hydrochloride, and the mixture was heated under reflux at 60°C. for 13 hours. Then, the acetone was distilled off, and the resulting reaction mixture was purified in the same manner as in Example 1 to obtain 13.3 g. of the intended product in the form of pale yellow liquid boiling at 75°–76°C./4 mmHg. Upon cooling, the liquid grew into crystals melting at 35°–36°C. Yield, 86%.

EXAMPLE 41.

40 ml. of Acetone was added to 15.4 g. of acetonine and 14.9 g. of pyridine nitrate, and the mixture was heated under reflux at 60°C. for 13 hours. Then, the acetone was distilled off, and the resulting reaction mixture was purified in the same manner as in Example 1 to obtain 13.2 g. of the intended product in the form of pale yellow liquid boiling at 75°–76°C./4 mmHg. Upon cooling, the liquid grew into crystals melting at 35°–36°C. Yield, 85%.

EXAMPLE 42.

60 ml. of Acetone was added to 15.4 g. of acetonine and 19.1 g. of triacetonamine hydrochloride, and the mixture was heated under reflux at 60°C. for 13 hours. Then, the acetone was distilled off, and the resulting reaction mixture was purified in the same manner as in Example 1 to obtain 28.6 g. of the intended product in the form of pale yellow liquid boiling at 75°–76°C./4 mm Hg. Upon cooling, the liquid grew into crystals melting at 35°–36°C. Yield, 85%.

EXAMPLE 43.

45 ml. of Acetone was added to 15.4 g. of acetonine and 12.5 g. of thiourea hydrochloride, and the mixture was heated under reflux at 60°C. for 13 hours. Then, the acetone was distilled off, and the resulting reaction mixture was purified in the same manner as in Example 1 to obtain 14.7 g. of the intended product in the form of pale yellow liquid boiling at 75°–76°C./4 mmHg. Upon cooling, the liquid grew into crystals melting at 35°–36°C. Yield, 95%.

EXAMPLE 44.

45 ml. of Acetone was added to 15.4 g. of acetonine and 12.7 g. of urea nitrate, and the mixture was heated under reflux at 60°C. for 13 hours. Then, the acetone was distilled off, and the resulting reaction mixture was purified in the same manner as in Example 1 to obtain 13.2 g. of the intended product in the form of pale yellow liquid boiling at 75°–76°C./4 mmHg. Upon cooling, the liquid grew into crystals melting at 35°–36°C. Yield, 85%.

EXAMPLE 45.

66 g. of a Dried hydrochloride of Amberlite IR-45 (product of Rhom & Haas Co.) was added to a solution of 5 g. of acetonine in 150 ml. of acetone, and the mixture was heated under reflux at 60°C. for 8 hours. Then, acetone was distilled off, and the resulting reaciton mixture was purified in the same manner as in Example 1 to obtain 4.3 g. of the intended product in the form of pale yellow liquid boiling at 75°–76°C./4 mmHg. Upon cooling, the liquid grew into crystals melting at 35°–36°C. Yield, 86%.

EXAMPLE 46.

60 ml. of Acetone was added to 21.4 g. of acetonine acetate, and the mixture was heated under reflux at 60°C. for 13 hours. Then, the acetone was distilled off. A saturated aqueous solution of potassium carbonate was added to the residue and the mixture was extracted with benzene. The extract was dried over anhydrous potassium carbonate, and benzene was distilled off. The residue was purified by distillation under reduced pressure to obtain 13.3 g. of triacetonamine in the form of pale yellow liquid boiling at 75°–76°C./4 mmHg. Upon cooling, the liquid grew into crystals melting at 35°–36°C. Yield, 86%.

EXAMPLE 47.

60 ml. of Acetone was added to 21.3 g. of a basic succinate of acetonine, synthesized from 2 moles of acetonine and 1 mole of succinic acid, and the mixture was heated under reflux at 60°C. for 13 hours. The acetone was distilled off, and the resulting reaction mixture was purified in the same manner as in Example 1 to obtain 13.3 g. of triacetonamine in the form of pale yellow liquid boiling at 75°–76°C./4 mmHg. Upon cooling, the liquid grew into crystals melting at 35°–36°C. Yield, 86%.

EXAMPLE 48.

80 ml. of Acetone was added to 27.2 g. of a neutral succinate of acetonine, the mixture was heated under reflux at 60°C. for 13 hours. Then, the acetone was distilled off, and the resulting reaction mixture was purified in the same manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 85%.

EXAMPLE 49.

65 ml. of Acetone was added to 21.2 g. of a basic maleate of acetonine, and the mixture was heated under reflux at 60°C. for 13 hours. Then, the acetone was distilled off, and the resulting reaction mixture was purified in the same manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 87%.

EXAMPLE 50.

80 ml. of Acetone was added to 27.6 g. of acetonine benzoate, and the mixture was heated under reflux at 60°C. for 13 hours. Then, the acetone was distilled off, and the resulting reaction mixture was purified in the same manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 85%.

EXAMPLE 51.

120 ml. of Acetone was added to 40.2 g. of acetonine o-iodobenzoate, and the mixture was heated under reflux at 60°C. for 13 hours. Then, the acetone was distilled off, and the resulting reaction mixture was purified in the sane manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 85%.

EXAMPLE 52.

90 ml. of Acetone was added to 29.0 g. of acetonine m-toluylate, and the mixture was heated under reflux at 60°C. for 13 hours. Then, the acetone was distilled off, and the resulting reaction mixture was purified in the same manner as in Example 1 to obtain 13.2 g. of triacetonamine in a form of pale yellow liquid boiling at 75°–76°C./4 mmHg. Upon cooling, the liquid grew into crystals melting at 35°–36°C. Yield, 85%.

EXAMPLE 53.

100 ml. of acetone was added to 33.2 g. of acetonine p-tert-butylbenzoate, and the mixture was heated under reflux at 60°C. for 13 hours. Then, the acetone was distilled off, and the resulting reaction mixture was purified in the same manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 85%.

EXAMPLE 54.

100 ml. of Acetone was added to 32.6 g. of acetonine p-toluenesulfonate, and the mixture was heated under reflux at 60°C. for 13 hours. Then, the acetone was distilled off, and the resulting reaction mixture was purified in the same manner as in Example 1 to obtain 13.9 g. of triacetonamine in the form of pale yellow liquid boiling at 75°–76°C./4 mmHg. Upon cooling, the liquid grew into crystals melting at 35°–36°C. Yield, 90%.

EXAMPLE 55.

90 ml. of Acetone was added to 30.2 g. of acetonine cinnamate, and the mixture was heated under reflux at 60°C. for 13 hours. Then, the acetone was distilled off, and the resulting reaction mixture was purified in the same manner as in Example 1 to obtain 13.2 g. of triacetonamine in the form of pale yellow liquid boiling at 75°–76°C./4 mmHg. Upon cooling, the liquid grew into crystals melting at 35°–36°C. Yield, 85%.

EXAMPLE 56.

6.3 g. of Acetonine hydrochloride was dissolved in a mixed solvent comprising 35 g. of methanol and 35 g. of acetone. The mixture was maintained at room temperature for 24 hours in a sealed equipment to effect the reaction. After completion of the reaction, the reaction mixture was purified in the same manner as in Example 1 to obtain triacetonamine in a yield of 127%.

EXAMPLE 57.

A solution of 19.2 g. of acetonine in 70 g. of acetone was added with 7 g. of methanol. Then, 0.9 g. of dry gaseous hydrogen chloride was introduced therein and absorbed. The solution was sealed and heated at 60°C. for 10 hours to effect the reaction. After completion of the reaction, the reaction mixture was purified in the same manner as in Example 1 to obtain triacetonamine in a yield of 140%.

EXAMPLE 58.

A solution of 6.3 g. of acetonine in 24 g. of acetone was added dropwise with 6.2 g. of methanol solution of hydrogen chloride (5%, by weight). The solution was heated at 60°C. for 10 hours in a sealed equipment to effect the reaction. After completion of the reaction, the reaction mixture was purified in the same manner as in Example 1 to obtain tiracetonamine in a yield of 147%.

EXAMPLE 59.

A solution of 6.3 g. of acetonine in a mixed solvent comprising 30 g. of acetone and 30 g. of methanol was added with 1.6 g. of methanesulfonic acid. The mixture was maintained at room temperature for 24 hours in a sealed equipment to effect the reaction. After completion of the reaction, the reaction mixture was purified in the same manner as in Example 1 to obtain triacetonamine in a yield of 95.3%.

EXAMPLE 60.

A solution of 6.3 g. of acetonine in a mixed solvent comprising 20 g. of acetone and 2 g. of ethanol was added with 0.5 g. of acetic acid. The mixture was heated at 60°C. for 10 hours in a sealed equipment to effect the reaction. After completion of the reaction, the reaction mixture was purified in the same manner as in Example 1 to obtain triacetonamine in a yield of 89.5%.

EXAMPLE 61.

Following the substantially same procedure as shown in Example 60 except that 0.63 g. of maleic acid was used in place of acetic acid, triacetonamine was obtained in a yield of 102%.

EXAMPLE 62.

A solution of 6.3 g. of acetonine in 40 g. of acetone was added with 0.5 g. of malonic acid and the mixture was heated at 60°C. for 10 hours in a sealed equipment to effect the reaction. After completion of the reaction, the reaction mixture was purified in the same manner as in Example 1 to obtain triacetonamine in a yield of 115%.

EXAMPLE 63.

A solution of 5.0 g. of acetonine in 21 g. of methanol was added with 19 g. of acetone and 4.0 g. of urea nitrate. The mixture was maintained at room temperature for 24 hours to effect the reaction. After completion of the reaction, the reaction mixture was purified in the same manner as in Example 1 to obtain triacetonamine in a yield of 125%.

EXAMPLE 64.

Following the substantially same procedure as in Example 63 except that 7.5 g. of urea p-toluenesulfonate was used in place of urea nitrate, triacetonamine was obtained in a yield of 110%.

EXAMPLES 65 – 67.

5.0 g. of Acetonine was dissolved in a mixed solvent comprising 19 g. of acetone and 9.5 g. of another solvent listed below. The solution was added with a catalyst listed below and the mixture was heated at 60°C. for 10 hours in a sealed equipment to effect the reaction. After completion of the reaction, the reaction mixture was purified in the same manner as in Example 1 to obtain triacetonamine in a yield as shown hereinbelow.

| No. of Example | Solvent | Catalyst | Amount used (g.) | Yield of triacetonamine (%) |
|---|---|---|---|---|
| 65 | dimethyl-formamide | ammonium chloride | 0.4 | 139 |
| 66 | dimethyl-sulfoxide | urea nitrate | 1.2 | 123 |
| 67 | methanol | ammonium p-toluene-sulfonate | 0.8 | 119 |

EXAMPLE 68.

A solution of 5.0 g. of acetonine in a mixed solvent comprising 19 g. of acetone and 1.9 g. of methanol was added with 1.5 g. of triacetonamine hydrochloride. The mixture was heated at 60°C. for 10 hours in a sealed equipment to effect the reaction. After completion of the reaction, the reaction mixture was purified in the same manner as in Example 1 to obtain triacetonamine in a yield of 115% deducting the amount of triacetonamine used as catalyst.

EXAMPLE 69.

A solution of 5.0 g. of acetonine in a mixed solvent comprising 19 g. of acetone and 9.5 g. of methanol was added with 1.3 g. of ammonium acetate. The mixture was maintained at room temperature for 24 hours in a sealed equipment to effect the reaction. After completion of the reaction, the reaction mixture was purified in the same manner as in Example 1 to obtain triacetonamine in a yield of 91.1%.

EXAMPLE 70.

A solution of 5.0 g. of acetonine in 40 g. of acetone was added with 1.6 g. of acetonine formate. The mixture was heated at 60°C. for 10 hours in a sealed equipment to effect the reaction. After completion of the reaction, the reaction mixture was purified in the same manner as in Example 1 to obtain triacetonamine in a yield of 95.8%.

EXAMPLE 71.

A solution of 15.4 g. of acetonine in 60 g. of acetone was added dropwise with 6.5 g. of boron trifluoride etherate at room temperature. After completion of the addition, the mixture was heated at 48°–50°C. for 3 hours to effect the reaction. After completion of the reaction, the reaction mixture was purified in the same manner as in Example 1 to obtain triacetonamine in a yield of 116%.

EXAMPLE 72.

5 g. of Acetonine and 12.4 g. of ammonium bromide were added to 30 g. of acetone and the mixture was maintained at room temperature for 38 hours to effect the reaction. After completion of the reaction, the reaction mixture was purified in the same manner as in Example 1 to obtain triacetonamine in a yield of 239%.

EXAMPLES 73 – 75.

A mixture of 1.0 g. of acetonine, 4.0 g. of acetone and 0.38 g. of ammonium bromide as catalyst was added with another catalyst listed below. The mixture was stirred at 40°C. in a flask fitted with a stopper, and the yield of triacetonamine was determined at regular intervals. The time required to obtain triacetonamine in a yield of 90% is shown hereinbelow.

| No. of Example | Another catalyst | Amount used (mg.) | Time (hrs.) |
|---|---|---|---|
| Control | — | — | 3.25 |
| 73 | sodium iodide | 59 | 2.25 |
| 74 | lithium iodide | 52 | 2.25 |
| 75 | iodine | 100 | 2.00 |

EXAMPLE 76.

A solution of 7.7 g. of acetonine in 15 ml. of ether was added dropwise with a solution of 8.1 g. of trichloroacetic acid in 15 ml. of ether at 5° – 10°C. under stirring.

After completion of the addition, the whole was stirred for 1 – 2 hours. Crystals thus precipitated were filtered, washed with ether and dried under reduced pressure to give 15.5 g. of acetonine trichloroacetate as colorless crystals melting at 113° – 114°C. Yield, 97.9%.

EXAMPLES 77 – 85.

Following the substantially same procedure as shown in Example 76, the following acetonine salts were obtained.

| No. of Example | Acetonine salt | Melting point (°C.) |
|---|---|---|
| 77 | acetonine p-tosylate | 115 – 117 |
| 78 | diacetonium sulfate | 166 – 168 |
| 79 | acetonine hydrochloride | 123 – 125 |
| 80 | acetonine dichloroacetate | 106 – 108 |
| 81 | acetonine acetate | 102 – 103 |
| 82 | acetonine formate | 66 – 68 |
| 83 | diacetonium maleate | 103 – 104 |
| 84 | acetonine benzoate | 117 – 118 |
| 85 | acetonine cinnamate | 115 – 117 |

What is claimed is:

1. A process for preparing triacetonamine, comprising reacting acetonine with a compound selected from the group consisting of acetone, diacetone alcohol and combinations thereof in the presence of at least 12.5 mol -% based on acetonine of an acid catalyst under anhydrous conditions.

2. The process according to claim 1 wherein acetonine is reacted with acetone in the presence of at least 12.5 mol-% based on acetonine of an acid catalyst under anhydrous conditions.

3. The process according to claim 1 wherein the acid catalyst is a salt of a proton acid with ammonia or a nitrogen-containing organic base.

4. The process according to claim 3 wherein a mineral acid or an organic acid or an inorganic acid is used as the proton acid.

5. The process according to claim 4 wherein a sulfonic or carboxylic acid is used as the organic acid.

6. The process according to claim 3 wherein the salt is an ammonium salt of a mineral acid.

7. The process according to claim 3 wherein the salt is an ammonium salt of an organic acid.

8. The process according to claim 3 wherein the salt is a salt of a nitrogen-containing organic base with a mineral acid.

9. The process according to claim 3 wherein the salt is a salt of a nitrogen-containing organic base with an organic acid.

10. The process according to claim 3 wherein the nitrogen-containing organic base is triacetonamine, triethylamine, hexamethylenediamine, 1,4-diazabicyclo[2,2,2]-octane, urea or thiourea.

11. The process according to claim 3 wherein the salt is a salt of hydrochloric, hydrobromic, hydroiodic or nitric acid or of an organic sulfonic or a halogenoacetic acid.

12. The process according to claim 3 wherein the salt is an ammonium salt of hydrochloric, hydrobromic, hydroiodic, nitric, benzenesulfonic, p-toluenesulfonic, methanesulfonic, dichloroacetic or trichloroacetic acid.

13. The process according to claim 3 wherein the salt is a salt of one of the acids selected from the group consisting of hydrochloric, hydrobromic, hydroiodic, nitric, benzenesulfonic, p-toluenesulfonic, methanesulfonic, dichloroacetic and trichloroacetic acid with one of the bases selected from the group consisting of triacetonamine, triethylamine, hexamethylenediamine, 1,4-diazabicyclo[2,2,2]-octane, urea and thiourea.

14. The process according to claim 3 wherein the salt is selected from the group consisting of ammonium chloride, ammonium bromide, ammonium iodide, ammonium formate, ammonium tosylate, urea nitrate, urea tosylate, thiourea hydrochloride, hexamethylenediamine dihydrochloride and triacetonamine hydrochloride.

15. The process according to claim 3 wherein the salt is hexamethylenediamine dihydrochloride.

16. The process according to claim 1 wherein the acid catalyst is an acid.

17. The process according to claim 16, wherein a Lewis acid is used as the acid.

18. The process according to claim 17 wherein the Lewis acid is boron trifluoride.

19. The process according to claim 16, wherein a proton acid is used as the acid.

20. The process according to claim 19 wherein a mineral acid or an organic acid is used as the proton acid.

21. The process according to claim 20, wherein a sulfonic or carboxylic acid is used as the organic acid.

22. The process according to claim 19 wherein the proton acid is hydrochloric acid, formic, acetic, malonic, succinic, maleic, benzoic, cinnamic acid, benzenesulfonic, or p-toluenesulfonic acid.

23. The process according to claim 16 wherein the acid is used in a stoichiometric ratio to acetonine.

24. The process according to claim 23 wherein the reaction is performed by using an acid adduct salt of acetonine and reacting it with the compound under anhydrous conditions.

25. The process according to claim 24 wherein the reaction is performed by using an acid adduct salt of acetonine, and reacting it with acetone under anhydrous conditions.

26. The process according to claim 24 wherein the acid adduct salt of acetonine is a salt of a proton acid.

27. The process according to claim 26 wherein the proton acid is a mineral acid or an organic acid.

28. The process according to claim 27, wherein a sulfonic or a carboxylic acid is used as the organic acid.

29. The process according to claim 26 wherein the acid adduct salt of acetonine is a salt of hydrochloric acid, formic, acetic, malonic, succinic, maleic, benzoic, cinnamic acid, benzenesulfonic, p-toluenesulfonic acid.

30. The process according to claim 1 wherein the reaction temperature is from 0° – 150°C.

31. The process according to claim 1 wherein the reaction temperature is from 30° – 150°C.

32. The process according to claim 1 wherein the reaction temperature is from 50° – 100°C.

33. The process according to claim 1 wherein the reaction temperature is from 10° – 110°C.

34. The process according to claim 1 wherein the reaction temperature is from 20° – 65°C.

35. The process according to claim 1 wherein the reaction is performed under pressure.

36. The process according to claim 35 wherein the pressure is from 1 – 30 atmospheres.

37. The process according to claim 35 wherein the pressure is from 1 – 10 atmospheres.

38. The process according to claim 35 wherein the pressure is from 1 – 3 atmospheres.

39. The process according to claim 1 wherein the reaction is performed in the presence of an organic solvent.

40. The process according to claim 39 wherein the solvent is a lower alcohol having from 1 – 4 carbon atoms or ethylene glycol monomethylether.

41. The process according to claim 40 wherein the lower alcohol used is methanol, ethanol, or a mixture of both.

42. The process according to claim 12 wherein the reaction is performed in acetone and a molar excess amount based on acetonine of the ammonium salt is used as an acid catalyst.

43. The process according to claim 1 wherein in addition to the acid catalyst, a different catalyst in an amount of 0.01 – 0.5 mol-% based on acetonine is used.

44. The process according to claim 43 wherein said different catalyst is selected from the group consisting of potassium iodide, sodium iodide, lithium bromide, lithium iodide, lithium thiocyanate, ammonium thiocyanate, lithium cyanide, lithium nitrate, ammonium sulfide, bromine, iodine, or the bromide, iodide, nitrate, methanesulfonate, benzenesulfonate or p-toluenesulfonate of ammonia, triethylamine, urea or thiourea.

* * * * *